United States Patent [19]

Sandler

[11] 4,063,024

[45] Dec. 13, 1977

[54] POLYOXYALKYLENE FLUOROALKYLTRIMELLITATES

[75] Inventor: Stanley Robert Sandler, Springfield, Pa.

[73] Assignee: Pennwalt Corporation

[21] Appl. No.: 722,178

[22] Filed: Sept. 10, 1976

Related U.S. Application Data

[62] Division of Ser. No. 596,779, July 17, 1975, Pat. No. 3,994,951.

[51] Int. Cl.$^2$ .................... C07C 69/76; C07C 103/24
[52] U.S. Cl. ...................................... 560/26; 260/404; 260/404.5; 560/42; 560/87
[58] Field of Search .......... 260/471 R, 471 C, 475 F, 260/472, 404, 404.5

[56] References Cited

U.S. PATENT DOCUMENTS 3,336,360  8/1967  Dill ....................................... 260/475

Primary Examiner—Paul M. Coughlan, Jr.
Assistant Examiner—Lisa Jones

[57] ABSTRACT

Novel polyoxyalkylene fluoroalkyltrimellitate compounds are disclosed that are useful for improving the soil release properties of textiles. These compounds may be conveniently prepared by reacting a fluorinated alkyl thiol or amine with trimellitic anhydride monoacid chloride to form a fluorinated trimellitic anhydride intermediate product which is then reacted with a polyoxyalkylene derivative.

14 Claims, No Drawings

POLYOXYALKYLENE FLUOROALKYLTRIMELLITATES

This is a division of application Ser. No. 596,779 filed July 17, 1975 now Pat. No. 3,994,951.

FIELD OF INVENTION

This invention relates to novel polyoxyalkylene fluoroalkyltrimellitate compounds and to the use of said compounds as, for example, textile soil release agents.

STATE OF THE PRIOR ART

In the past, fabrics have frequently been made soil- or stain releasing (hereinafter simply called soil releasing) by treating them with various fluorochemical polymers and copolymers containing hydrophilic components. Unfortunately such treatments have also rendered the fabrics water repellent and/or have decreased the water absorption properties. Both of these effects result in discomfort to a garment wearer.

A well-known commercial soil-release finish FC-218 (Dual-Action-Scotchgard) is known to contain fluorochemical polymers and polyoxyalkylene groups or segments, to render fabrics, such as cotton or 65/35 polyester-cotton oil and water repellent (see U.S. Pat. Nos. 3,503,915, 3,574,791, and 3,816,167), and to decrease the water absorption properties of treated fabrics.

SUMMARY OF THE INVENTION

The soil releasing compounds of this invention likewise contain fluorochemical and polyoxyalkylene groups, but surprisingly and desirably these compounds also impart significantly improved water absorption and wicking properties.

This invention concerns:

A. Compounds of the formula:

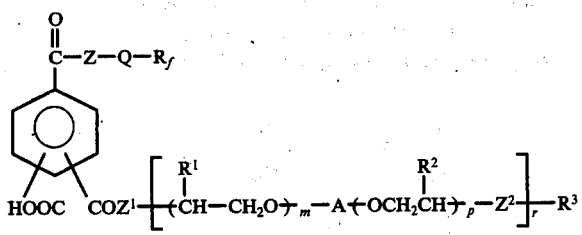

wherein:
The ring is 1,3,4 tri-substituted.
Z, $Z^1$ and $Z^2$ are independently selected from O, S or NR where R is H or an alkyl of 1-4 carbon atoms such as methyl, propyl or butyl.

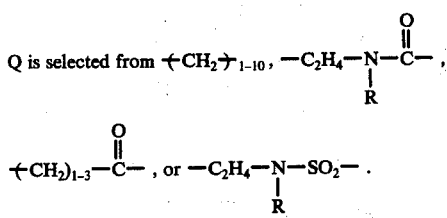

$R^1$ and $R^2$ are moieties independently selected from hydrogen or an alkyl of 1-4 carbons such as methyl, ethyl, or butyl. Within the segments of $m$ and $p$ repeating units, $R^1$ and $R^2$ are one or more of these moieties as is true for certain copolymers of alkylene oxides.

$m$ and $p$ are independent integers from 0 to 30 describing repeating units of polyoxyalkylene groups that form a chain with at least one polyoxyalkylene chain of at least three repeating units being present.

$R_f$ is selected from the group consisting of a linear or branched perfluoroalkyl, a linear or branched monochloroperfluoroalkyl or a linear or branched perfluoroisoalkoxyalkyl wherein each member of the group has 3 to 20 carbon atoms.

$r$ is an integer from 1 to 10.

A is a linking radical selected from the group consisting of the acyl segment of aliphatic or aromatic polycarboxylic acids, aliphatic or aromatic anhydrides or aliphatic or aromatic polycarbamic acids, a linear alkylene radical of 2 to 12 carbon atoms, or a cyclic or brached alkylene group of 3 to 12 carbon atoms.

$R^3$ is selected from H, $-\overset{O}{\overset{\|}{C}}-NH_2$, an alkyl having 1 to 20 carbon atoms, $R_f-Q-Z-\overset{O}{\overset{\|}{C}}-$

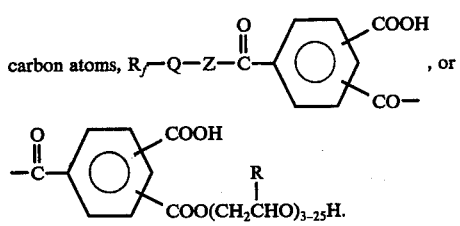

B. Processes for
1. treating substrates with the novel polyoxyalkylene fluoroalkyltrimellitate compounds to provide soil releasing properties; and
2. treating textiles with a combination of durable press agents and the novel polyoxyalkylene fluoroalkyltrimellitates to provide improved soil releasing properties with water absorption and wicking properties.

DETAILED DESCRIPTION OF INVENTION

The novel polyoxyalkylene fluoroalkyltrimellitates are prepared by first reacting fluorinated alkyl thiols, alcohols, or amines at about 100° to 190° C. with trimellitic anhydride monoacid chloride, preferably in the absence of catalysts, to give a fluorinated trimellitic anhydride intermediate product; then the intermediate product is directly reacted with polyoxyalkylene derivatives to give the desired carboxylic trimellitates.

The acid chloride group of trimellitic anhydride monoacid chloride reacts preferentially with the fluorinated alcohol, thiol or amine and thus leaves essentially intact the reactive anhydride group for reaction with the polyoxyalkylene derivatives. (Fluorinated mercaptans must be reacted first with trimellitic anhydride monoacid chloride since they do not substantially react with the aromatic anhydride group in the absence of catalysts. The order of the reaction with a fluorinated alcohol or fluorinated amine is not as critical as with the fluorinated mercaptans because the fluorinated alcohol and amine can be made to react with the anhydride; hence, the polyoxyalkylene derivative may be reacted first and the resulting anhydride group then reacted with the alcohol or amine.) Lewis-Acid catalysts can be used to accelerate the rate and lower the temperature for the reaction of the acid chloride with the alcohol or thiol.

Useful fluorinated mercaptans, alcohols and amines are represented by $R_fQZ$ where suitable $R_f$—groups are:

$F(CF_2)_n$—, where $n$ is 3 to 20,
$(CF_3)_2CF(CF_2)_m$—, where $m$ is 2 to 17,
$(CF_2Cl)(CF_3)CF(CF_2)_m$—, where $m$ is 2 to 17,
$(CF_3)_2CFO(CF_2)_m$—, where $m$ is 2 to 17, and
$CF_3CF_2(OCF_2CF_2)_p$—, where $p$ is 1 to 9.

Particularly preferred $R_f$ species are those where $m$ is 4 to 8 and $n$ is 6 to 10, for example, $(CF_3)_2CF(CF_2)_4$—,
$(CF_3)_2(CF(CF_2)_6$—,
$(CF_3)_2CF(CF_2)_8$—,
$F(CF_2)_6$—,
$F(CF_2)_8$—, and
$F(CF_2)_{10}$—.

Other specific examples of suitable $R_f$ groups are:

$F(CF_2)_3$—
$F(CF_2)_{10}$—
$F(CF_2)_{20}$—
$(CF_3)_2CF(CF_2)_2$—
$(CF_3)_2CF(CF_2)_8$—
$(CH_3)_2CF(CF_2)_{17}$—
$(CF_2Cl)$ $(CF_3)$ $(CF_2)_2$—
$(CF_2Cl)$ $(CF_3)$ $CF(CF_2)_8$—
$(CF_2Cl)$ $(CF_3)$ $CF(CF_2)_{17}$—
$(CF_3)_2CFO(CF_2)_2$—
$(CF_3)_2CFO(CF_2)_8$—
$(CF_3)_2CFO(CF_2)_{17}$—
$CF_3CF_2(OCF_2CF_2)_1$—
$CF_3CF_2(OCF_2CF_2)_9$—

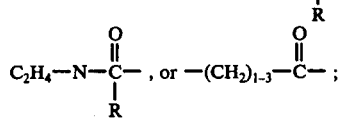

R is H or a lower alkyl having 1 to 4 carbon atoms. Some specific examples of Q are:

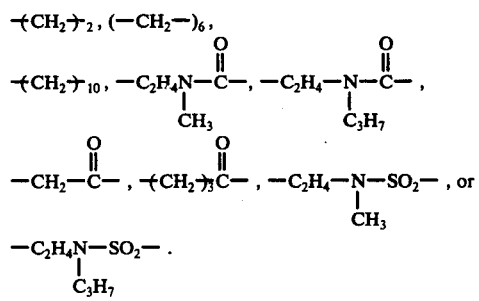

Particularly useful fluorinated mercaptans, alcohols and amines are those represented by $R_f(CH_2)_yXH$ where:

X is either S, O, or NR,
y is an integer from 2 to 10, preferably 2 or 3, and
$R_f$ is as described above.

Alcohols or mercaptans derived from the tetrafluoroethylene oligomers described in the British Patent No. 1,082,127, and mercaptans derived from polyperfluoropropylene oxide derivatives, such as described in U.S. Patent No. 2,912,018, are also suitable.

Z, $Z^1$ and $Z^2$ are independently selected from the group consisting of O, S or NR.

Representative polyoxyalkylene derivatives useful in preparing the compounds of this invention are:

1. Polyoxyethylene glycols, $HO(CH_2CH_2O)_nH$, where $n$ varies, depending on the molecular weight.

These glycols are sold under the Trademark, Carbowax, with a number as part of the mark, such as, Carbowax-400 or Carbowax-600. The number after the Trademark denotes the average molecular weight of the compound. These glycols are supplied by the Union Carbide Company.

2. Mixed polyoxyethylene and polyoxypropylene glycols,

where R is either $CH_3$ or H. These compounds are sold under the name Pluronic polyols supplied by BASF Wyandotte, 3. Polyoxyethylene amines, $H_2N(CH_2CHRO)_nR^1$—$NH_2$, where R is H and/or $CH_3$, and $R^1$ is an alkylene group. These compounds are marketed under Trademark, Jeffamine, supplied by Jefferson Chemicals.

4. Polyoxyalkylated alcohols, $HO(CH_2CH_2O)_nR$ where R is $CH_3$ (the methoxy Carbowax products) or

5. Polyoxyethylene polyols, $[HO(CH_2CH_2O)_n]_{3-4}R$ where R is a tri- or tetravalent alkyl group (the Pluracol products supplied by BASF Wyandotte).

It should be noted that the preferred polyoxyalkylene glycols are the polyoxyethylene glycols and especially preferred are those having a molecular weight of 400 to 1000. The use of polyols of higher molecular weight than those specified results in unsatisfactory soil release performance after multiple launderings.

Representative linking groups A are:

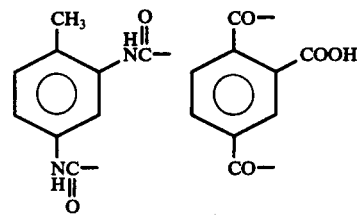

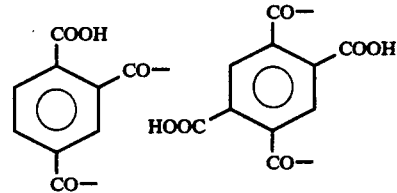

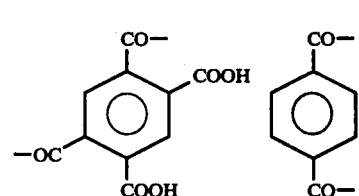

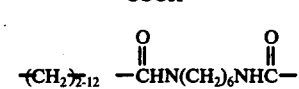

-continued
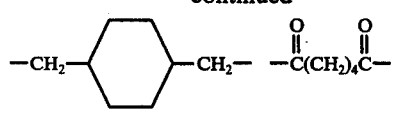
The following compounds are examples of the preferred soil-releasing compounds. (Note that various isomers are probably present in the reaction mass when making the following compounds because of variations in the relative reaction rates of the ingredients; however, these isomers do not detract from the usefulness of the compounds.)
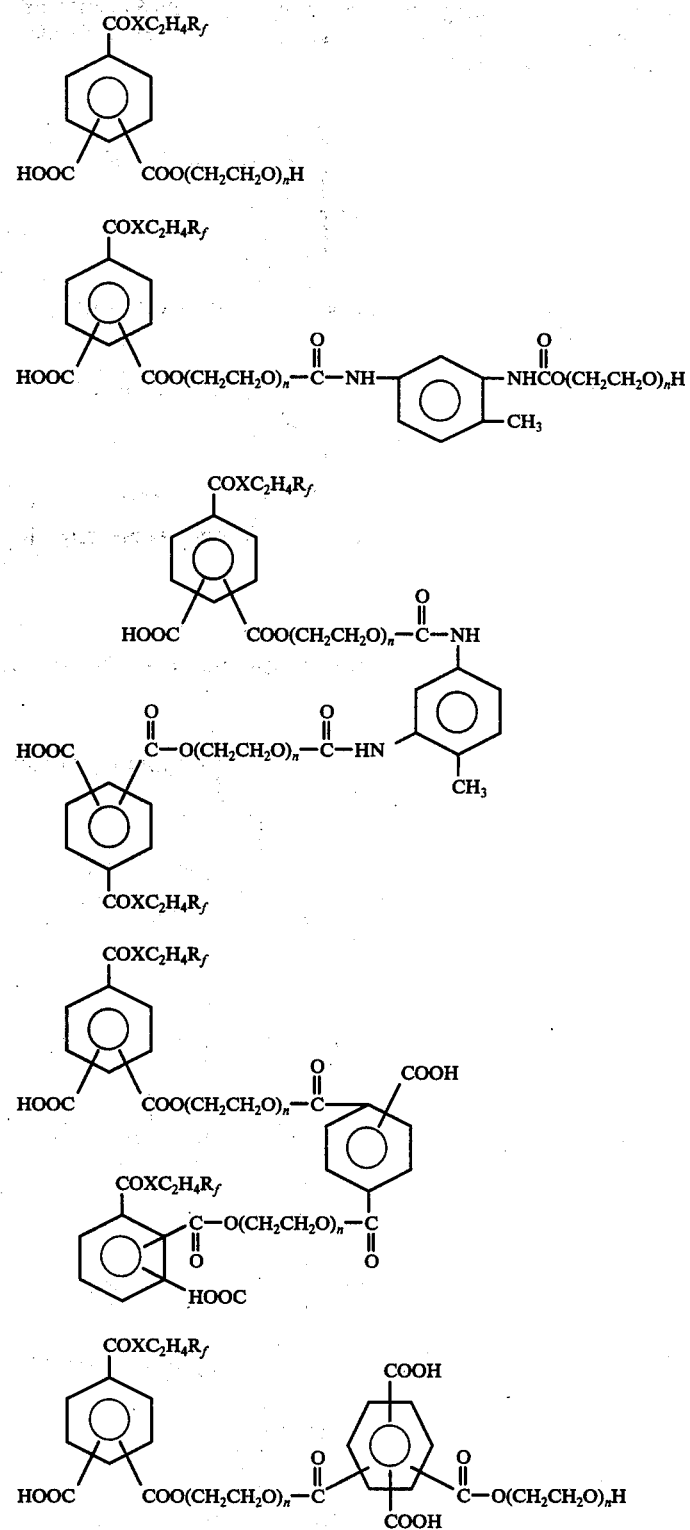

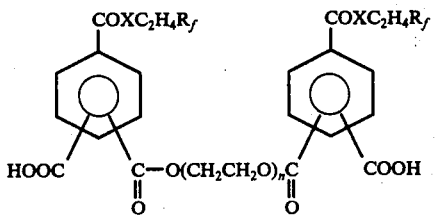
In all the above examples of the preferred soil-releasing compounds X is O or S, $n$ is 9 to 25 and $R_f$ is $-(CF_2)_y-CF(CF_3)_2$ wherein $y$ is 2 to 8.
Other examples of the novel soil releasing compositions are set forth below:
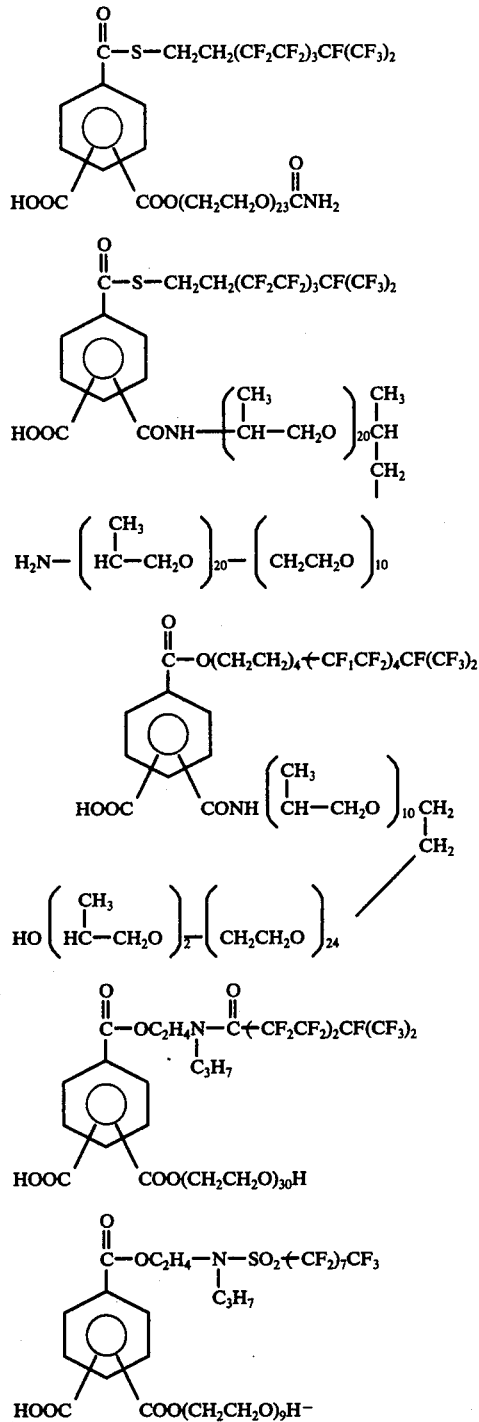

-continued
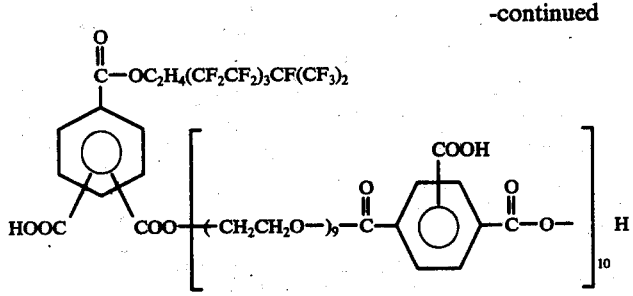
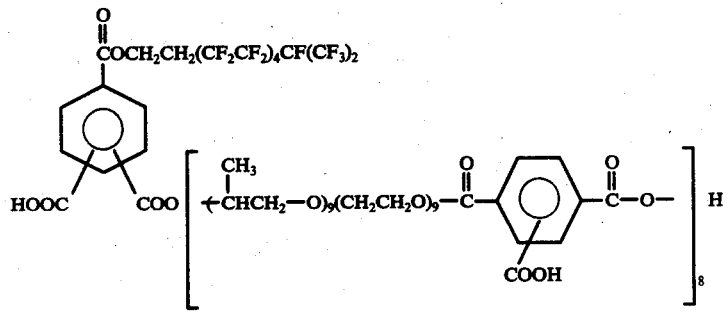
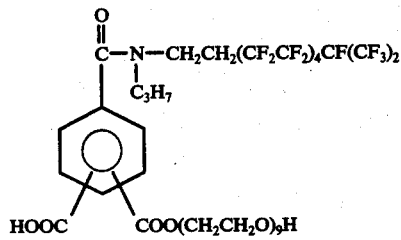
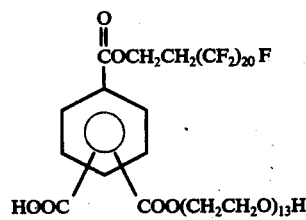
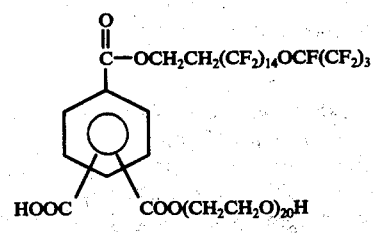
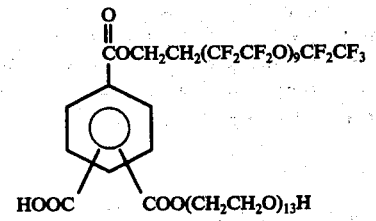
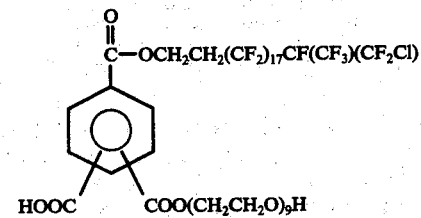

-continued

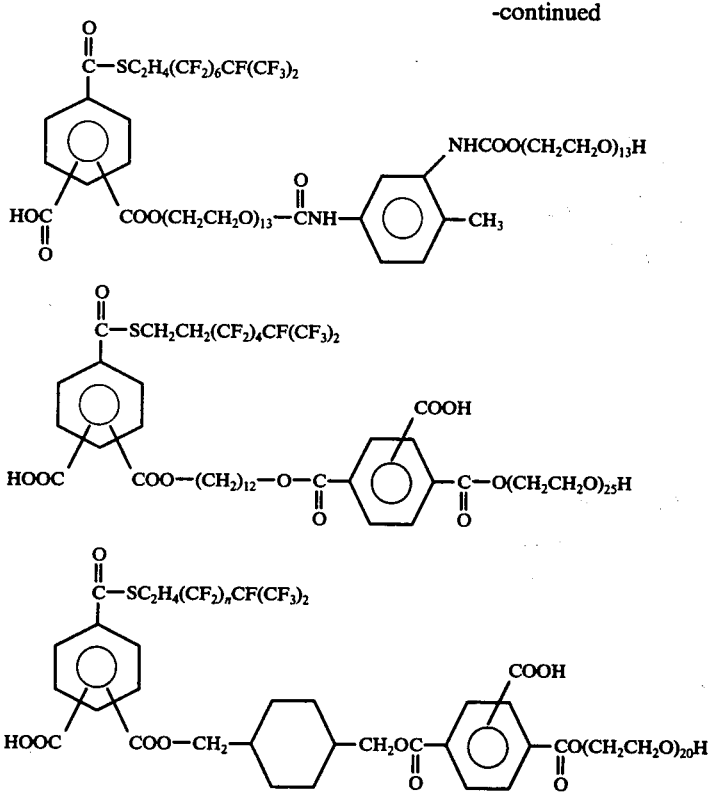

(this compound is a mixture wherein n is 4, 6 and 8 forming a mixture in the ratio of 1:1:1)

The polyoxyalkylene fluoroalkyltrimellitate compounds of this invention impart oil repellency and resistance to soiling of a variety of substrates such as: textiles, glass, paper, wood, leather, fur, asbestos, bricks, concrete, metals, ceramics, plastics, and plaster. Derivatives can be made that contain nitrogen, bromine, or phosphorus and that can impart flame retardant properties as well. By virtue of the available carboxylic acid group, the compounds of the invention can be used as intermediates to prepare or modify various systems such as synthetic resins and polymers. Also, the low surface-tension properties of the compounds of this invention in both aqueous and non-aqueous systems suggest their use as antifoams and leveling agents.

In the treatment of fabrics, the novel trimellitates of this invention may be applied in admixture with other treating agents, such as durable press resins, softeners, sizes, water repellents, flame retardants, and anti-static agents. The instant compounds are easily dispersed in water and can be readily applied by standard procedures to fabrics; for example, in a one-bath system with durable press resins. The durable press reagents are selected from aminoplasts, reaction products of formaldehyde and polyamino compounds, such as dimethylol dihydroxyethylene urea, dimethylol propylene urea, dimethylol ethylene urea, urea derivatives, carbamates, triazones, melamines, sulfones, acrolien derivatives, acetals and epoxy derivatives. Additionally, catalysts may be added to the compound to promote the cross-linking reaction.

All of the novel compounds in the treatment of the fabrics were applied to either 50/50 or 65/35 polyester-cotton(white) from aqueous pad baths using two dips and two nips to give a wet pick-up of about 60–70% corresponding to a fluorine loading of 0.104 to 0.129% owf. The fabrics were dried for 3.5 minutes at 110° C and cured for two minutes at 175° C.

In the following examples, stain removal is evaluated by visual observation using Test Method 130-1969 as described in the Technical Manual of the American Association For Textile Chemists and Colorists (AATCC), Howes Publishing Co., 44 E. 23rd St., New York, with overhead lighting arranged as described in the test procedure. The fabrics are stained with butter, Wesson Oil, Nujol, and mustard; then they are washed according to this procedure and placed on a black table top in front of a viewing board having "standard" specimens as shown in the following table:

Table 1

| Rating | Appearance |
| --- | --- |
| 5 | negligible or no staining (excellent cleanability) |
| 4 | slightly stained (good cleanability) |
| 3 | noticeably stained (fair cleanability) |
| 2 | considerably stained (poor cleanability) |
| 1 | heavily stained (very poor cleanability) |

The fabrics are evaluated for oil repellency by AATCC Test Method 118-1972 and for water absorbency by AATCC Test Method 79-1972.

The following examples illustrate the subject invention but are not in limitation thereof:

EXAMPLE 1 (PREPARATION OF INTERMEDIATE PRODUCT FTTA)

To a 3-neck, round-bottom flask is added 210.5 g (1.0 mole) of trimellitic anhydride monoacid chloride and 530 g (1.0 mole) of $(CF_3)_2CF(CF_2)_6CH_2CH_2SH$. The mixture is warmed with stirring at 170°–190° C for 3–4 hours or until all the hydrogen chloride evolution ceases and product obtained as a 95% yield of the perfluorothioltrimellitic anhydride (FTTA), mp 98–100° C (recrystallized from 50:50 benzene/ligroin).

Anal. Calcd. for $C_{20}H_7F_{19}SO_4$: C, 32, 43; H, 0.99; F, 51.28; S, 4.54. Found: C, 33.96; H, 1.14; F, 50.70; S, 4.50. Nmr analysis shows 3 aromatic protons and 4 aliphatic protons in the field strength areas consistent with the structure:

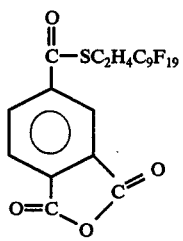

EXAMPLE 2

To 704 g (1.0 mole) of the product of Example 1 is added 400 g (1.0 mole) Carbowax 400 (Union Carbide) all at once and the mixture heated for 3 hours at 100°–190° C. The desired product is isolated in essentially quantitative yield. Calcd. mol. wt. 1104; found 1192. The analytical data (IR, $H^1$nmr and $F^{19}$nmr) are consistent with the assigned structure:

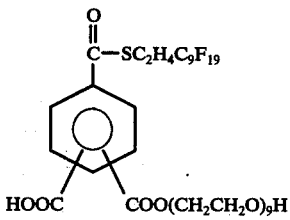

EXAMPLES 3-13

(The following preparations were carried out as in Example 2 using the reactants set forth below.)

| EX. NO. | FTTA from | Reactants | | PRODUCT STRUCTURE |
|---|---|---|---|---|
| 3 | Example 1 1.0 mole | Diol (2 mole) | (d) $CH_3$—C$_6$H$_3$(NHCOO(CH$_2$CH$_2$O)$_9$H)(NHCOO(CH$_2$CH$_2$O)$_9$H) (based on 2,4-toluene diisocyanate and Carbowax 400). | [structure: HOOC–C$_6$H$_3$(COO(CH$_2$CH$_2$O)$_9$–C(O)–NH–C$_6$H$_3$(CH$_3$)–NHCOO(CH$_2$CH$_2$O)$_9$H)(C(O)–SC$_2$H$_4$C$_9$F$_{19}$)] |
| 4 | Example 1 2.0 moles | Same as in Example 3 above | | [structure: HOOC–C$_6$H$_3$(COO(CH$_2$CH$_2$O)$_9$–C(O)–NH–C$_6$H$_3$(CH$_3$)–NHCOO(CH$_2$CH$_2$O)$_9$–C(O)–C$_6$H$_3$(COOH)(SC$_2$H$_4$C$_9$F$_{19}$))(C(O)–SC$_2$H$_4$C$_9$F$_{19}$)] |

| EX. NO. | FTTA from | Reactants | PRODUCT STRUCTURE |
|---|---|---|---|
| | Example 1 | Diol (1 mole) | |

-continued
EXAMPLES 3-13
(The following preparations were carried out as in Example 2 using the reactants set forth below.)
5    2.0 moles    Carbowax 600
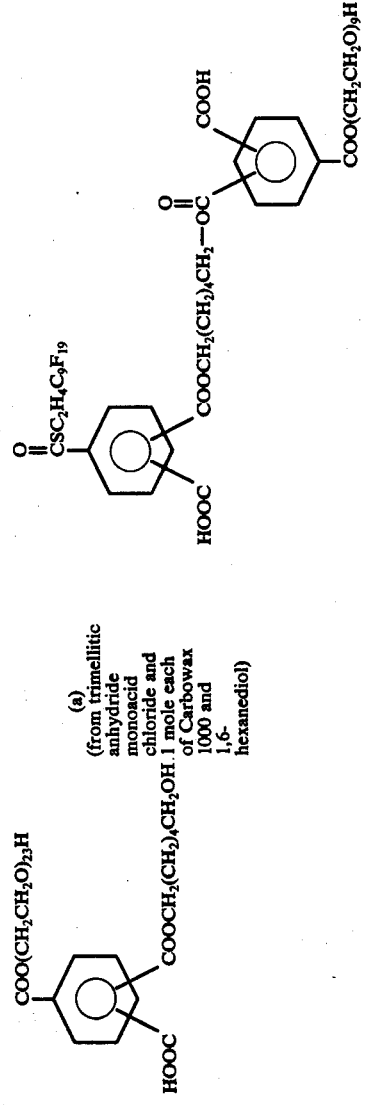
6    1 mole    (a)
(from trimellitic anhydride monoacid chloride and 1 mole each of Carbowax 1000 and 1,6-hexanediol)

-continued
EXAMPLES 3–13
(The following preparations were carried out as in Example 2 using the reactants set forth below.)
| | | (b) |
|---|---|---|
| 7 | 2.0 moles  | (from trimellitic anhydride mono-acid chloride and 2 moles of Carbowax 400) 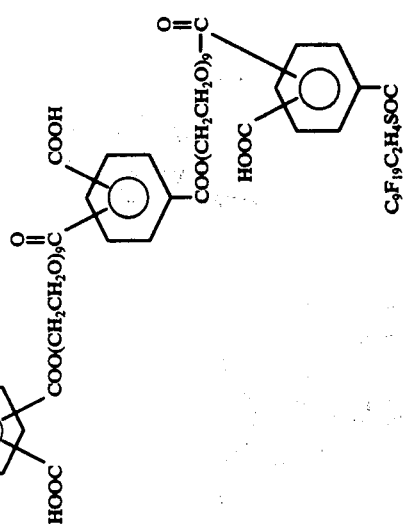 |
| 8 | 1.0 mole Same as Example 7 | 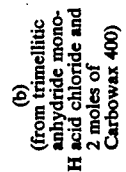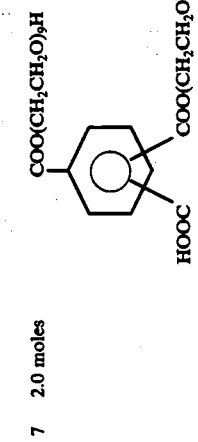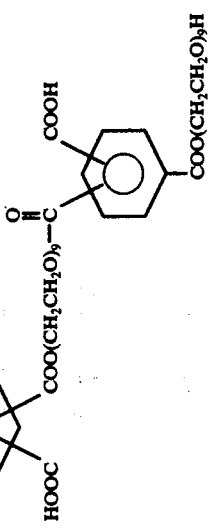 |

-continued
EXAMPLES 3-13
(The following preparations were carried out as in Example 2 using the reactants set forth below.)
| | | | |
|---|---|---|---|
| 9 | 2.0 mole | Carbowax 400 (c) | 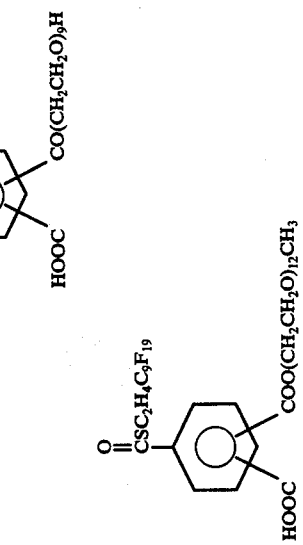 |
| 10 | 1.0 mole | 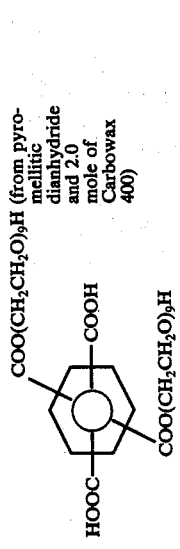 COO(CH$_2$CH$_2$O)$_9$H (from pyromellitic dianhydride and 2.0 mole of Carbowax 400) | 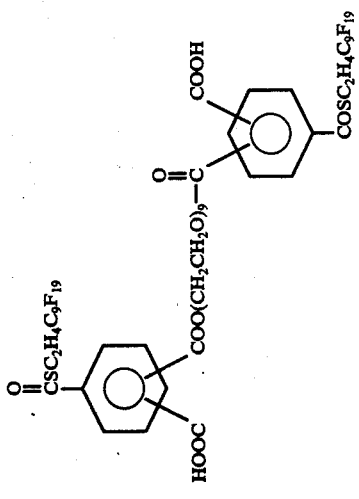 |
| 11 | 1.0 mole | Methoxy Carbowax 550 | |

-continued
EXAMPLES 3-13
(The following preparations were carried out as in Example 2 using the reactants set forth below.)
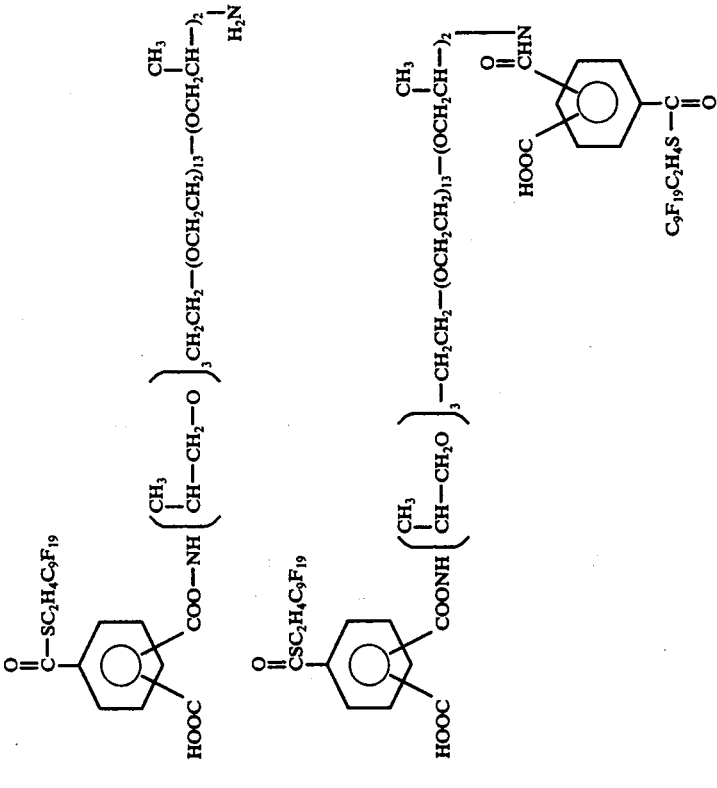
| | | |
|---|---|---|
| 12 | 1.0 mole | Jeffamine ED600 |
| 13 | 2.0 mole | Jeffamine ED600 |
Footnotes:
(a) Mol. wt. Calcd. 1980; found 1961 (Example 6)
(b) Mol. wt. Calcd. 2382; found 2497 (Example 7)
(c) Mol. wt. Calcd. 1808; found 2107 (Example 9)
(d) Mol. wt. Calcd. 2382; found 2890 (Example 3)

EXAMPLE 14

To a 3-neck, round-bottom flask is added 210.5 g (1.0 mole) of trimellitic anhydride monoacid chloride and 514 g (1.0 mole) of $(CF_3)_2CF(CF_2)_6CH_2CH_2OH$. The mixture is heated together at 170° C for 3 hours or until all the hydrogen chloride evolution ceased. Then 400 (1.0 mole) of Carbowax 400 is added and heated at 100°–190° C for 3 hours to give the product in essentially quantitative yield.

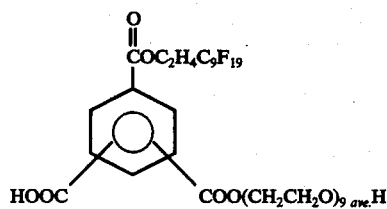

EXAMPLE 15

This example describes a preparation using a less-preferred molecular weight Carbowax starting material:

In a 3-neck, round-bottom flask is prepared 35.0 g (0.05 mole) perfluorothioltrimellitic anhydride as in Example 1. Then 100 g (0.025 mole) of Carbowax 4,000 is added and the mixture heated for 3 hours at 170°–190° C. The product is isolated in 99% yield (134 g) and has the following structure:

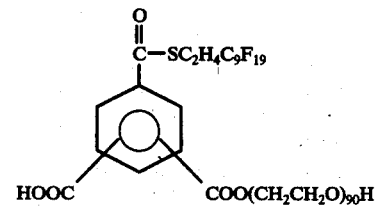

EXAMPLE 16

To 465 g (0.42 mole) of the product of Example 2 is added 45 q (0.506 mole) of diethylcarbamate, 946 ml. of toluene and 10 ml. of Tyzor TBT catalyst (tetrabutyl titanate). The mixture is refluxed and the ethanol azeotrope removed at 90–100° C. After the reaction is complete, the solvent is removed under reduced pressure to a low volume and the product washed with fresh toluene in order to extract away the remaining catalyst. The toluene is finally completely removed and the product obtained in quantitative yield. The structure of the product is:

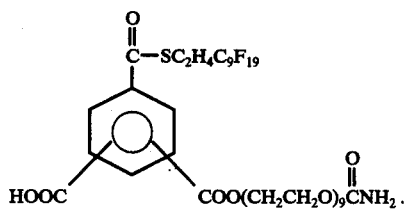

EXAMPLE 17

To one mole of Carbowax-400 is added at once 1.0 mole of the following mixture:

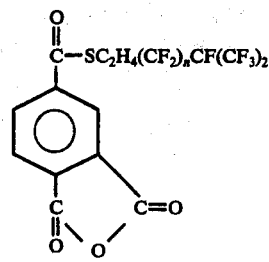

wherein n is 4, 6 and 8 for the mixture in a ratio of 1:1:1 when prepared as set forth in Example 1. The reactants are heated for 3 hours at 100°–190° C. The desired product, isolated in essentially quantitative yield, is a mixture having the following structure:

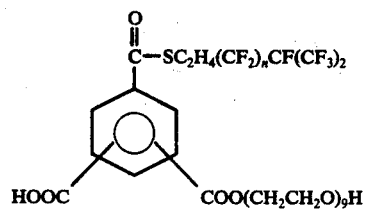

8 for the components of the mixture in a ratio of 1:1:1.

The compounds described in Examples 2–15 are rated for utility as soil-release agents using the test described earlier. The results are:

TABLE II

| Composition of Example No. | Soil-Release Ratings[a] 1 Wash | 5 Wash | Oil Repellency[b] 1 Wash |
|---|---|---|---|
| Control (no soil release) | 1.5 | 1.3 | 0 |
| 2 | 3.7 | 2.7 | 5–6 |
| 3 | 3.7 | 3.0 | 5 |
| 4 | 3.3 | 3.1 | 5 |
| 5 | 3.9 | 2.4 | 5 |
| 6 | 3.4 | 3.0 | 5 |
| 7 | 4.0 | 3.1 | 5 |
| 8 | 3.0 | 2.1 | 5 |
| 9 | 3.1 | 2.3 | 5 |
| 10 | 3.0 | 2.7 | 5 |
| 11 | 3.1 | 2.1 | 5 |
| 12 | 3.2 | 3.1 | 3–4 |
| 13 | 3.4 | 2.9 | 5 |
| 14 | 3.6 | 2.2 | 5 |
| 15 | 2.7 | 1.6 | 3 |
| Commercial soil release FC-218 of 3M Co. | 3.7–4.0[b] | 2.6–3.1[b] | 5–6 |

[a]The values shown are the average soil release ratings for both fabrics using 4 stains.
[b]Over a testing period of 6 months, FC-218 treated samples varied within the limits shown.
[c]Oil repellency values are the average for two fabrics.

The oil repellency ratings of the compositions of this invention thus compare favorably to the commercial fluorochemical soil-release (FC-218 of 3M Co.) and are far superior than the control.

The compounds described in Examples 2 to 15 and the commerical soil-release sample are rated for their water absorbency (wicking). The results are:

TABLE III

| Composition of Example No. | Water Absorbency (time in seconds to be completely absorbed by fabrics) | |
|---|---|---|
| | 65/35 Polyester/Cotton | 50/50 Polyester/Cotton |
| FC-218 (3M Co.) | 600+[a] | 600+[a] |
| 2 | 37 | 22 |
| 3 | 10 | 10 |
| 4 | 25 | 20 |
| 5 | 22 | 12 |
| 6 | 9 | 13 |
| 7 | 20 | 19 |

TABLE III-continued

| Composition of Example No. | Water Absorbency (time in seconds to be completely absorbed by fabrics) | |
| --- | --- | --- |
| | 65/35 Polyester/ Cotton | 50/50 Polyester/ Cotton |
| 8 | 28 | 29 |
| 9 | 29 | 25 |
| 10 | 3 | 2 |
| 11 | 10 | 7 |
| 12 | 1 | 1 |
| 13 | 10 | 6 |
| 14 | 88 | 32 |
| 15 | 14 | 16 |

*Test arbitrarily terminated at this point.

The water absorbency data for fabrics treated with the compounds of this invention are seen to be far superior to a commercial soil-release agent, FC-218, at the same fluorine loading on the weight of the fabric.

Having described the invention:

1. A compound of the formula:

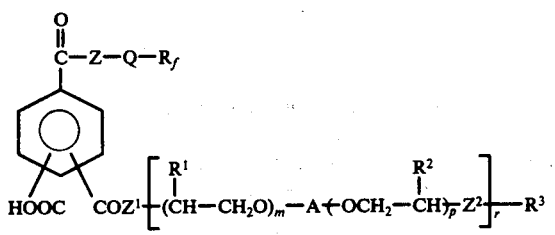

wherein:

a. the ring is 1, 3, 4 tri-substituted,
b. Z is O, $Z^1$ is selected from O or NR, and $Z^2$ is selected from O, S or NR where R is H or an alkyl of 1–4 carbon atoms, c) Q is selected from $(CH_2-)_{1-10}$,

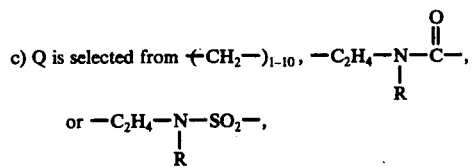

d. $R^1$ and $R^2$ are moieties independently selected from hydrogen or an alkyl having 1 to 4 carbon atoms,
e. m and p are independent integers from 0 to 30 describing repeating units of polyoxyalkykene groups that form a chain with at least one polyoxyalkylene chain of at least three repeating units being present.
f. $R^1$ and $R^2$ are one or more of said moieties within the repeating units m and p,
g. $R_f$ is selected from the group consisting of a linear or branched perfluoroalkyl, a linear or branched monochloroperfluoroalkyl or a linear or branched perfluoroisoalkoxyalkyl wherein each member of the group has 3 to 20 carbon atoms,
h. r is an integer from 1 to 10,
i. A is a linking group selected from the group consisting of the acyl segment of alkanoic or mono or dicyclic aromatic polycarboxylic acids, alkanoic or mono or dicyclic aromatic anhydrides or alkanoic or mono or dicyclic carbomates, linear alkylene of 2 to 12 carbon atoms or a cyclic alkylene of 5–8 carbon atoms or a branched alkylene of 3–12 carbon atoms, and
j. $R^3$ is selected from H or an alkyl of 1 to 20 carbon atoms.

2. The compound of claim 1 wherein $R_f$ is $(CF_3)CF(CF_2)_{4-8}$—.
3. The compound of claim 1 wherein $R_f$ is $CF_3(CF_2)_{2-9}$—.
4. The compound of claim 1 wherein $R_f$ is $CF_3CF_2(OCF_2CF_2)_{1-3} OCT_2CF_2$—.
5. The compound of claim 1 wherein R is $(CF_3)_2CFO(CF_2)_{4-8}$—.
6. The compound of claim 1 wherein Q is $(-CH_2-)_{1-10}$.
7. The compound of claim 1 where Q is

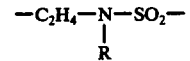

where R is an alkyl group having 1 to 4 carbon atoms.

8. The compound of claim 1 where the polyoxyalkylene chains are polyethylene oxides.
9. The compound of claim 1 where the polyoxyalkylene chains are copolymers of ethylene oxide and propylene oxide.
10. The compound of claim 1 where the linking group A is a trimellitate derivative.
11. The compound of claim 1 wherein the linking group A is a poloxyethylene trimellitate.
12. The compound of claim 1 where the linking group A is a poloxyalkylene pyromellitate.
13. The compound of claim 1 wherein the linking group is a polyoxyalkylene toluene dicarbamate.
14. The compound of claim 1 where $R^3$ is H.

* * * * *